United States Patent [19]

Twentier

[11] 3,949,740
[45] Apr. 6, 1976

[54] DISPOSABLE SPECULUM FOR TYMPANIC THERMOMETER

[75] Inventor: Max E. Twentier, Phoenix, Ariz.

[73] Assignee: Products International Marketing, Phoenix, Ariz.

[22] Filed: Dec. 16, 1974

[21] Appl. No.: 533,138

Related U.S. Application Data

[62] Division of Ser. No. 390,687, Aug. 23, 1973, Pat. No. 3,878,836.

[52] U.S. Cl. ................................................. 128/9
[51] Int. Cl.² ........................................... A61B 1/22
[58] Field of Search ......................... 128/3, 6, 4, 9

[56] References Cited
UNITED STATES PATENTS

| 411,160 | 9/1889 | Maloney | 128/4 |
|---|---|---|---|
| 1,727,495 | 9/1929 | Wappler | 128/6 |
| 2,797,684 | 6/1957 | Moore | 128/9 |
| 3,146,775 | 9/1964 | Moore et al. | 128/6 |
| 3,596,653 | 8/1971 | Hotchkiss | 128/9 |
| 3,698,387 | 10/1972 | Moore et al. | 128/9 |

Primary Examiner—Robert W. Michell
Assistant Examiner—Henry S. Layton
Attorney, Agent, or Firm—Christie, Parker & Hale

[57] ABSTRACT

A disposable plastic speculum is used on an infrared sensing thermometer used by placing it in the patient's ear for sensing body temperature through the tympanic membrane. The speculum has the general shape of a funnel with relatively shallow and relatively steep tapered frustoconical sections. The speculum is placed on a speculum retainer on the thermometer for use. The exterior of the speculum retainer has the general shape of interior of the speculum and includes a peripheral enlargement near its smaller end. When the speculum is placed on the retainer it is stretched by the enlargement and thereby retained in place. The speculum is made of a plastic having limited resistance to stress cracking so that the stretched portion over the enlargement cracks during retention on the speculum retainer. Since the speculum thus inherently destroys itself, it is assured that the speculum will be discarded and a new one used for each patient.

5 Claims, 6 Drawing Figures

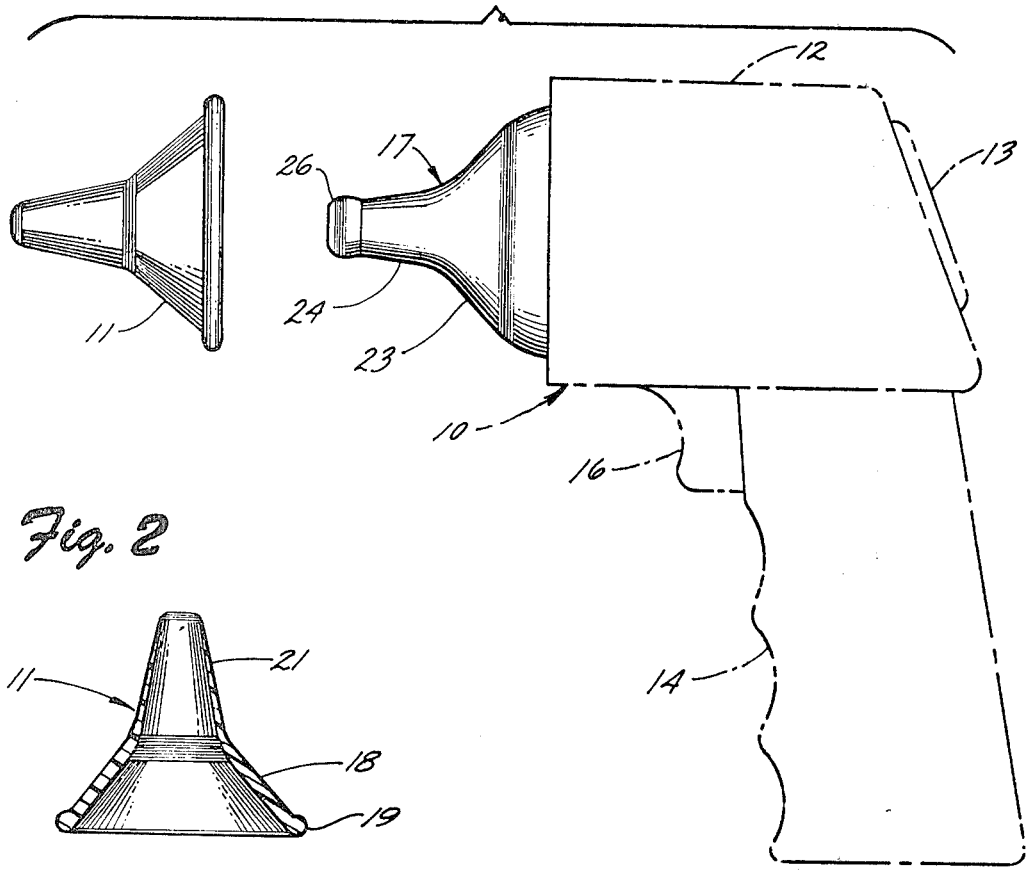
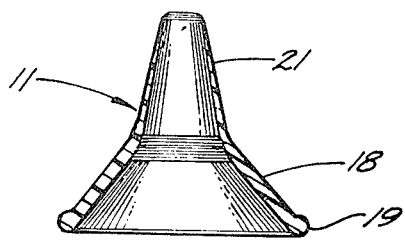
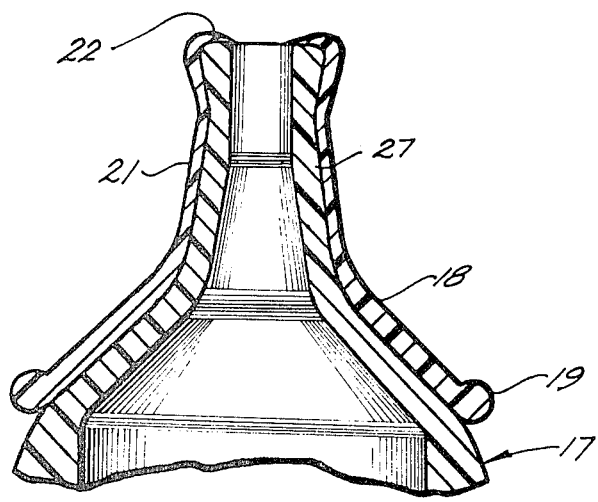
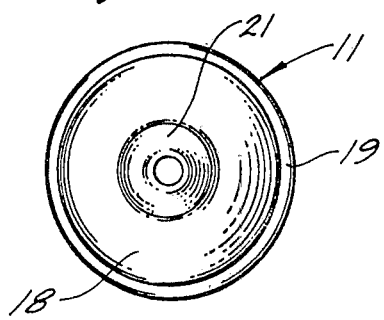

DISPOSABLE SPECULUM FOR TYMPANIC THERMOMETER

This is a division of Application Ser. No. 390,687, filed Aug. 23, 1973, now U.S. Pat. No. 3,878,836.

BACKGROUND

It has been proposed to measure temperature of the human body by way of the ear rather than the mouth or rectum as is most commonly done. Oral thermometers have several noticeable hazards of significant concern to hospital and clinic personnel. If the thermometer is broken in the patient's mouth, as can readily happen with children or elderly persons, the patient may ingest mercury or glass fragments. Further, if thermometers are not thoroughly sterilized between uses communicable diseases may be transmitted from one patient to another. Oral thermometers have the additional disadvantage that they only approximate deep body temperature since the patient may have ingested cooling or warming materials which mask the true temperature.

Oral thermometers are of limited usefulness with infants and rectal thermometers are commonly used. Many serious accidents have occurred due to breakage of the thermometer during such use. In addition, both oral and rectal thermometers are subject to high breakage rates during normal handling. Both oral and rectal thermometers take a substantial time interval to come to temperature equilibrium and the time of valuable health personnel is often wasted during the wait for equilibrium. If the personnel are rushed, inadequate time may be allotted and the thermometer may not have reached equilibrium when the reading is made.

To overcome these difficulties, measurement of body temperature through the ear has been proposed. One such instrument places a thermistor in intimate thermal contact with the interior of the ear. A preferred instrument employs an infrared sensor which detects radiation from within the ear. The infrared sensors are optical instruments requiring an unobstructed "light" path between the sensor and the region where temperature sensing is desired. Such a technique is advantageous since the tympanic membrane is substantially transparent to infrared radiation and the temperature measured is effectively that of the carotid artery which passes in close proximity to the tympanic membrane. Such an infrared sensor is very rapid and comes to equilibrium within seconds. A suitable technique is disclosed in U.S. Pat. No. 3,282,106.

When such a tympanic thermometer employing an infrared sensor is used, it is desirable to insert an end portion into the ear canal so that temperature of the surroundings does not influence the reading obtained. Such a tympanic thermometer is used for many patients much as an otoscope or other ear examining instrument. It has often been the practice to simply wipe the tip of the speculum that enters the patient's ear with alcohol between patients to effect limited sterilization and remove any wax that may have been deposited. Although the likelihood of cross contamination from one patient to another through the ear is very low, it is preferable that a clean speculum be used for each patient.

It is therefore desirable to provide a speculum that is sufficiently inexpensive that it can be disposed of between usages. Preferably, the speculum should have a limited lifetime so that medical personnel do not continue to use the same speculum, and in effect are forced to dispose of it between successive patients. Such a speculum cover should be inexpensive, non-contaminating, non-irritating, and maintain a fixed optical path for the infrared radiation to the sensor.

BRIEF SUMMARY OF THE INVENTION

There is, therefore, provided in practice of this invention according to a presently preferred embodiment, a disposable speculum for use with a speculum retainer having a generally conical tip with a peripheral enlargement thereon. The speculum is a generally conical sheath of elastically stretchable plastic having a relatively larger open end and relatively smaller open end with an elastically stretchable portion adjacent the relatively smaller open end with sufficient strength to be installed on a speculum retainer at least once and sufficiently susceptible to stress cracking to rupture during retention on the speculum retainer due to stretching by the enlargement.

DRAWINGS

These and other features and advantages of the present invention will be appreciated as the same becomes better understood by reference to the following detailed description of a presently preferred embodiment when considered in connection with the accompanying drawings wherein:

FIG. 1 illustrates in exploded view a tympanic thermometer and speculum constructed according to principles of this invention;

FIG. 2 is a longitudinal cross-section of the speculum;

FIG. 3 is an end view of the speculum;

FIG. 4 is a longitudinal cross-section of the speculum on a speculum retainer;

DESCRIPTION

Figure 6:
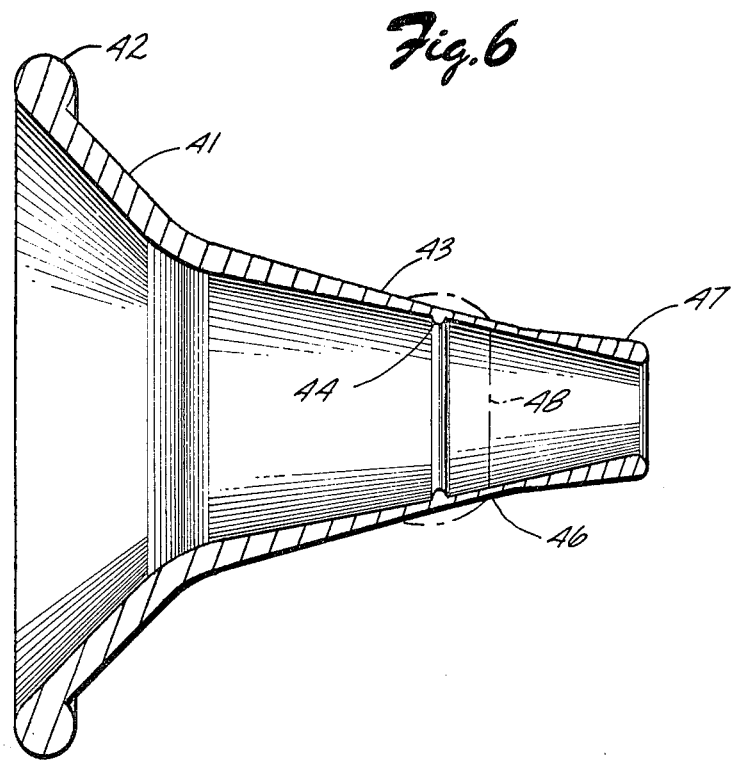
FIG. 6 is a longitudinal cross-section of another embodiment of speculum constructed according to principles of this invention.

FIG. 1 illustrates in phantom a representative tympanic thermometer 10 and, exploded therefrom, a speculum 11 constructed according to principles of this invention. The thermometer has an instrument housing 12 for mounting a conventional infrared sensor, power supplies, electronic circuits and the like, none of which need be separately illustrated herein. A dial, electroluminescent or other suitable indicator 13 is mounted on the housing for showing the temperature sensed. A hand grip handle 14 is used for holding the instrument and a trigger 16 is used for actuating it. A speculum retainer 17 on the housing receives the speculum 11 when the instrument is used.

When it is desired to use the thermometer, the speculum is placed on the retainer and inserted in the patient's ear. The trigger is depressed, thereby actuating the infrared sensor and electronic circuitry associated therewith, and within no more than a few seconds the patient's temperature is shown on the indicator. Preferably, this is shown as a digital display for minimizing reading errors by the operator. The speculum is then discarded and a new speculum installed for the next patient.

The speculum 11 has the general shape of a funnel with a first hollow, generally frustoconical base section 18 having a relatively shallow taper. An enlarged bead 19 is formed around the relatively larger open end of the base section. The base section 18 blends gradually into a second hollow generally frustoconical nose or tip section 21 having a relatively steep taper. As best seen in FIG. 2, the base section 18 has a relatively greater wall thickness and the wall thickness of the nose section 21 gradually decreases towards its smaller open end. A small turned-in lip 22 is present at the smaller tip end of the speculum to shield the end of the retainer from deposits of ear wax. Any wax deposits are discarded with the disposable speculum.

The speculum retainer 17 has an exterior profile substantially complementary to the interior profile of the speculum with one exception. The retainer has a base section 23 flaring outwardly and approximately complementary to the interior of the base section 18 of the speculum. The retainer also has a more nearly cylindrical frustoconical nose section 24 complementary in general to the interior of the nose section 21 of the speculum. The exterior of the retainer differs from the interior of the speculum by having a peripheral enlargement 26 adjacent its smaller open end. The speculum retainer is hollow as seen in FIG. 4, to provide an optical path for infrared radiation. As seen in FIG. 4, when the speculum is pressed onto the speculum retainer into a position wherein its base portion 18 is in engagement with the base portion 23 of the retainer, the wall of the speculum near its tip is stretched to fit over the enlargement 26. This stretching of the speculum makes the properties of the plastic of which the speculum is formed of importance.

The speculum retainer has a reduced diameter portion 27 between the enlargement 26 and its base portion. Stretching of the plastic speculum over the enlargement occurs as it is installed on the retainer. The stretching is well within the elastic range of the plastic and the portion inwardly from the tip (that is, nearer the base of the speculum) contracts after passage over the enlargement, thereby lightly gripping the retainer. The taper of the nose portion of the retainer is not sufficient for causing the speculum to creep off over the enlargement since this would entail stretching of the plastic that has contracted into the reduced diameter portion 27. It is also desirable that the interior of the speculum be very slightly roughened for inhibiting such creeping. Thus, once the speculum is installed on the retainer, it remains in place until manually dislodged. In order to remove the speculum, all one needs do is press forwardly on the bead 19 and the speculum pops off readily.

The plastic of which the speculum is formed must be sufficiently elastically stretchable that the stretching of the wall as it passes over the enlargement of the retainer does not exceed the fast tensile strength of the plastic. This keeps the speculum from cracking when it is installed on the retainer.

Many plastics are susceptible to what is known as stress cracking. Stress cracking occurs when the plastic is subjected to tensile stress for a period of time. Thus, a stress-relieving crack may occur in the plastic when it is maintained under a stress appreciably below its fast tensile strength. The susceptibility of a plastic to stress cracking can be measured by ASTM Test Method D-2561. It is desirable that the plastic of which the speculum is formed have an appreciable susceptibility to stress cracking so that after it has remained in a stretched condition on the enlargement for a period of time, a crack spontaneously develops. This spontaneous cracking provides a self-destruct feature for the speculum so that the medical personnel using it are induced to discard the speculum rather than re-using it for more than one patient. Such stress cracking should occur in no more than a few minutes on the retainer so that it will not be reused several times before discarding.

Preferably, the speculum is formed of polyethylene with a relatively low melt index (ASTM Test Method D-1238). In polyethylene and many related thermoplastic materials, the susceptibility to stress cracking is related to the melt index so that the higher the melt index the greater the resistance to stress cracking.

It is found that to form a suitable speculum, the plastic should have a resistance to stress cracking not greater than that of polyethylene having a melt index of less than about 30 gm/10 min. It is found with such resistance to stress cracking that a crack ordinarily appears in the speculum adjacent the peripheral enlargement on the retainer within one or two minutes. This is ample time for taking and even rechecking a patient's temperature. If a plastic having a greater resistance to stress cracking is employed, the naturally occurring self-destruction of the speculum may be unduly prolonged so that the speculum is used for multiple patients. The crack that forms is ordinarily only in the region of stretching and does not propagate to both ends of the speculum.

The time until stress cracking occurs is also dependent upon the wall thickness of the speculum adjacent the peripheral enlargement. If the wall is made too thick, cracking may occur as soon as the speculum is installed. It is therefore important that the wall be sufficiently thin that it can tolerate a peripheral enlargement of about 20% without exceeding the fast tensile strength of the plastic. This permits it to be safely installed without cracking over a peripheral enlargement that causes a 20% elongation. It will be noted that plastics of these properties often have an elongation at rupture in a fast tensile test (ASTM Test Method D-638) of as much as 100%.

A particularly suitable plastic for forming the speculum is equivalent to a polyethylene available from Rexene Polymers Company, a division of Dart Industries, Inc., under their trade designation Rexene PE 207C. This is a polyethylene having a melt index of about 22 gm/10 min and a density of about 0.925. A speculum made of such a material (with small addition of a conventional slip additive for mold release) can be rapidly and economically formed by injection molding. Such a speculum can be installed on a retainer with 20% peripheral elongation without immediate cracking. Cracking does occur, however, within no more than a few minutes after installation, thereby inducing disposal of the speculum. It will also be noted that if a speculum is placed on the retainer, removed, then reinstalled, cracking seems to occur sooner, thereby inhibiting re-use of specula that may have been ejected before actual cracking occurred.

Figure 5:
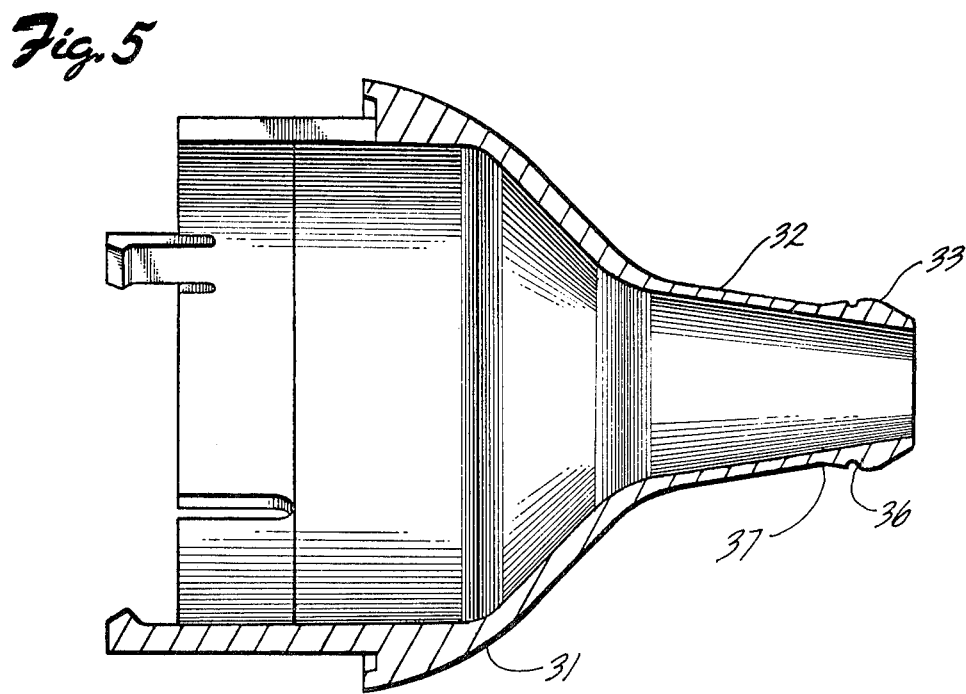
FIG. 5 is a longitudinal cross-section of another embodiment of the speculum retainer.

FIG. 5 illustrates in longitudinal cross-section a slightly different embodiment of speculum retainer. As hereinabove described, this speculum retainer also has a base portion 31 and nose portion 32 with a hollow interior for passage of infrared radiation. A peripheral enlargement 33 is provided adjacent the smaller open end and differs to the extent that the maximum diameter of the enlargement is set back from the tip slightly further than in the above-described embodiment. Thus, at the tip of the speculum retainer, there is a conical section 34 with an included angle of about 60°. In addition, a shallow locking groove 36 is provided on the outside of the retainer between the point of maximum diameter of the enlargement and the reduced diameter portion 37 spaced inwardly from the tip.

FIG. 6 illustrates in longitudinal cross-section an embodiment of speculum connectable to the slightly modified retainer of FIG. 5. This embodiment of speculum also has a generally funnel shape with most elements substantially the same as hereinabove described. The speculum has a frustoconical base portion 41 with peripheral bead 42 at its open larger end. The smaller end of the base portion blends into a tapered nose portion 43. The wall thickness of the nose portion 43 decreases gradually from the base portion to a point where a small internal ridge 44 is formed. Forwardly from the ridge 44 there is a short section 46 wherein the wall thickness is substantially uniform and is typically about 15 to 20 mils thick. Thereafter, extending forwardly, there is a section 47 wherein the wall thickness gradually increases to provide greater stiffness.

When the speculum of FIG. 6 is installed on the retainer of FIG. 5, it fits much in the manner hereinabove described and the end of the retainer reaches approximately to a line 48 illustrated in phantom in FIG. 6. This brings the ridge 44 within the speculum into engagement with the groove 36 on the outside of the retainer. The portion of the speculum where the ridge occurs is somewhat stretched, as seen in phantom in FIG. 6, and the cooperation between it and groove further inhibit inadvertant ejection of the speculum from the retainer. It will also be noted from the phantom lines in FIG. 6 that the section 46 having uniform wall thickness is stretched over the enlargement on the retainer. This stretching of the speculum induces stress cracking in the manner hereinabove described for self-destruction of the speculum.

The somewhat stiffened extension 47 on the speculum beyond the end of the retainer serves as a guide as the instrument is inserted in the ear of the patient. The enlargement is such that, on most patients, intrusion of the speculum into the ear is limited by contact with the bony structure. The end portion 47 of the speculum may extend somewhat further into the ear for shielding the retainer from contamination by waxes or the like. Any wax that may be picked up on the end of the speculum is thus discarded with the disposable speculum. The extending tip 47 also provides a somewhat longer optical path within the instrument and apparently retards heat transfer for assuring accurate temperature measurement. The end portion beyond the stretchable section 46 is preferably somewhat thicker to enhance stiffness in this region and prevent collapse of the speculum in case it is somewhat twisted within the ear. If the speculum were to collapse, portions of it could enter the optical path of the infrared radiation and interfere with temperature measurement.

Although limited embodiments of speculum and retainer for a tympanic thermometer have been described and illustrated herein, may modifications and variations will be apparent to one skilled in the art. Thus, for example, although the speculum is particularly useful in an instrument for measuring temperature in the ear of a patient, it is also quite suitable for use on an otoscope or other ear examining instrument. Similar arrangements of speculum for entering other body orifices will be apparent.

If desired for enhanced self-destruction, a peripherally extending notch may be provided in the speculum for propagation of the stress crack. Due to the direction of stressing as the speculum is stretched over the enlargement, it is found that the stress crack occurs in a longitudinal direction. A peripherally extending notch may cause propagation of the crack in a peripheral direction further inducing medical personnel to discard the speculum after each patient. Many other modifications and variations will be apparent to one skilled in the art and it is therefore to be understood that within the scope of the appended claims the invention may be practiced otherwise than as specifically described.

What is claimed is:

1. A combination of a speculum retainer and a speculum, the speculum retainer comprising a rigid member having an axial interior passage and a generally frustoconical exterior with a peripheral enlargement nearer its smaller end and a reduced cross-section portion between the enlarged portion and the wider portion of the exterior;

the speculum comprising a generally frustoconical plastic member having a principal portion interiorly complementary to the exterior of the retainer and a minor portion elastically stretchable to conform to the enlargement without exceeding the fast tensile strength of the plastic in the stretched portion of the speculum, and wherein the stretching of the speculum by the enlargement induces stress cracking in the speculum in no more than a few minutes.

2. A combination of a speculum retainer and a speculum, the speculum retainer comprising a rigid member having an axial interior passage and a generally frustoconical exterior with a peripheral enlargement nearer its smaller end and a reduced cross-section portion between the enlarged portion and the wider portion of the exterior;

the speculum comprising a generally frustoconical plastic member formed of a plastic having a resistance to stress cracking not greater than polyethylene having a melt index of less than about 30, and having a principal portion interiorly complementary to the exterior of the retainer and a minor portion elastically stretchable to conform to the enlargement without exceeding the fast tensile strength of the plastic in the stretched portion of the speculum; and wherein the peripheral enlargement is sufficiently larger than the minor portion of the speculum that it induces stress cracking in the speculum in no more than a few minutes.

3. A disposable speculum as defined in claim 2 wherein the extending portion comprises an inwardly directed lip adjacent the smaller end of the speculum for covering the end of the retainer.

4. A combination comprising:

a disposable speculum including a first hollow, generally frustoconical base section having a relatively shallow taper; a second hollow generally frustoconical nose section having a relatively steep taper, the base of the nose section being essentially a continuation of the smaller end of the base section; said nose section being formed of a plastic having a resistance to stress cracking not greater than polyethylene having a melt index of less than about 30 and sufficiently thin relatively nearer its small end to have a peripheral elongation of about 20% without exceeding the fast tensile strength of the plastic; and a speculum retainer in the form of a rigid member having an axial interior passage and a generally frustoconical exterior with a peripheral enlargement nearer its smaller end and a reduced cross section portion between the enlarged portion and the wider portion of the exterior, the exterior of the rigid member being complementary to the interior of the disposable speculum except for the peripheral enlargement which has a larger diameter than the speculum for elastic stretching thereof and wherein the peripheral enlargement is sufficiently larger than the speculum that it induces stress cracking in the speculum in no more than a few minutes.

5. A combination as defined in claim 4 wherein the speculum includes a portion extending beyond the end of the retainer for inhibiting contamination thereof.

* * * * *